(12) United States Patent
Gerard et al.

(10) Patent No.: US 11,197,657 B2
(45) Date of Patent: Dec. 14, 2021

(54) METHODS AND SYSTEMS FOR IDENTIFYING ULTRASOUND IMAGES

(71) Applicant: General Electric Company, Schenectady, NY (US)

(72) Inventors: Olivier Gerard, Oslo (NO); Elina Sokulin, Tirat Carmel (IL); Svein Arne Aase, Trondheim (NO)

(73) Assignee: General Electric Company, Schenectady, NY (US)

( * ) Notice: Subject to any disclaimer, the term of this patent is extended or adjusted under 35 U.S.C. 154(b) by 740 days.

(21) Appl. No.: 15/643,045

(22) Filed: Jul. 6, 2017

(65) Prior Publication Data
US 2019/0008480 A1 Jan. 10, 2019

(51) Int. Cl.
| | |
|---|---|
| *A61B 8/08* | (2006.01) |
| *G06T 7/00* | (2017.01) |
| *G06F 3/0481* | (2013.01) |
| *A61B 8/00* | (2006.01) |
| *A61B 90/00* | (2016.01) |

(52) U.S. Cl.
CPC .......... *A61B 8/5246* (2013.01); *A61B 8/5223* (2013.01); *G06F 3/04817* (2013.01); *G06T 7/0012* (2013.01); *A61B 8/0808* (2013.01); *A61B 8/0875* (2013.01); *A61B 8/0883* (2013.01); *A61B 8/0891* (2013.01); *A61B 8/4444* (2013.01); *A61B 8/463* (2013.01); *A61B 8/465* (2013.01); *A61B 8/5269* (2013.01); *A61B 8/56* (2013.01); *A61B 2090/365* (2016.02)

(58) Field of Classification Search
None
See application file for complete search history.

(56) References Cited

U.S. PATENT DOCUMENTS

| | | | |
|---|---|---|---|
| 5,148,809 A * | 9/1992 | Biegeleisen-Knight | A61B 8/488 348/163 |
| 6,979,294 B1 * | 12/2005 | Selzer | A61B 5/02007 600/450 |
| 2011/0125527 A1 | 5/2011 | Nair | |
| 2013/0072781 A1 | 3/2013 | Omernick et al. | |
| 2014/0204242 A1 * | 7/2014 | Anderson | G06F 19/321 348/231.5 |
| 2016/0121142 A1 * | 5/2016 | Zhang | G06T 7/248 600/439 |
| 2016/0331349 A1 * | 11/2016 | Abe | A61B 8/0883 |

* cited by examiner

*Primary Examiner* — Angela M Hoffa
*Assistant Examiner* — Younhee Choi (57) ABSTRACT

Systems and methods generally relate to identifying ultrasound images from multiple ultrasound exams. The systems and methods identify a first ultrasound image feature of a current ultrasound image of an anatomical structure during a current ultrasound exam based on ultrasound data received from an ultrasound probe, and accessing a plurality of prior ultrasound images that were acquired during a prior ultrasound exam. The systems and methods compare the first ultrasound image feature in the current ultrasound image with related ultrasound image features in the plurality of prior ultrasound images to identify candidate ultrasound images. The systems and methods identify a resultant ultrasound image from the candidate ultrasound images based on the related ultrasound image features, and display the current and resultant ultrasound images on a display.

18 Claims, 5 Drawing Sheets

METHODS AND SYSTEMS FOR IDENTIFYING ULTRASOUND IMAGES

FIELD

Embodiments described herein generally relate to identifying ultrasound images from multiple ultrasound exams.

BACKGROUND OF THE INVENTION

During an ultrasound exam a series of ultrasound images (e.g., over fifty images) are acquired. The clinician (e.g., sonographer, doctor, nurse) will regularly want to compare a select ultrasound image of a current ultrasound exam with a corresponding ultrasound image acquired during prior ultrasound exams. The clinician compares ultrasound images between ultrasound exams to monitor physiological, pathological, and/or function changes in the patient over time. The clinician selects one of the prior ultrasound images that matches the select ultrasound image, which is a labor and time intensive manual process.

BRIEF DESCRIPTION OF THE INVENTION

In an embodiment, a method (e.g., for identifying an ultrasound image between ultrasound exams) is provided. The method includes identifying a first ultrasound image feature of a current ultrasound image of an anatomical structure during a current ultrasound exam based on ultrasound data received from an ultrasound probe, and accessing a plurality of prior ultrasound images that were acquired during a prior ultrasound exam. The method includes comparing the first ultrasound image feature in the current ultrasound image with related anatomical features in the plurality of prior ultrasound images to identify candidate ultrasound images. The method includes identifying a resultant ultrasound image from the candidate ultrasound images based on the related ultrasound image features, and displaying the current and resultant ultrasound images on a display.

In an embodiment, a system (e.g., a medical imaging system) is provided. The system includes an ultrasound probe configured to acquire ultrasound data of an anatomical structure, a display, and a controller circuit. The controller circuit is configured to identify a first ultrasound image feature of a current ultrasound image of the anatomical structure during a current ultrasound exam based on ultrasound data received from an ultrasound probe, access a plurality of prior ultrasound images that were acquired during a prior ultrasound exam, compare the first ultrasound image feature in the current ultrasound image with related ultrasound image features in the plurality of prior ultrasound images to identify candidate ultrasound images, identify a resultant ultrasound image from the candidate ultrasound images based on the related ultrasound image features, and display the current and resultant ultrasound images on the display.

In an embodiment, a method (e.g., for identifying an ultrasound image between ultrasound exams) is provided. The method includes identifying a first ultrasound image feature of a current ultrasound image of an anatomical structure during a current ultrasound exam based on ultrasound data received from an ultrasound probe. The first ultrasound image feature includes at least one of an anatomical measurement graphic, an ultrasound image mode, an anatomical feature, a view window, a noise of the current ultrasound image, or an acquisition setting. The method includes accessing a plurality of prior ultrasound images of the anatomical structure that were acquired during a prior ultrasound exam, comparing the first ultrasound image feature with related ultrasound image features in the plurality of prior ultrasound images to identify candidate ultrasound images, and determining a first set of characteristic vectors for the first ultrasound image and sets of related characteristic vectors for the plurality of prior ultrasound images. The candidate ultrasound image is identified based on the first and related sets of characteristic vectors. The method includes identifying first and second resultant ultrasound images from the candidate ultrasound images based on the related ultrasound image features, and displaying the current, the first resultant, and the second resultant ultrasound images on the display.

DETAILED DESCRIPTION OF THE INVENTION

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments described herein generally relate to identifying ultrasound images between different ultrasound exams. The imaging medical system describe herein compares the current ultrasound image in real-time with prior ultrasound images acquired during prior ultrasound exams as the current ultrasound image is being acquired and/or reviewed by the clinician. For example, the imaging medical system is configured to analyze the current ultrasound image to identify a view window (VW) of the current ultrasound image. Simultaneously and/or concurrently, the medical imaging system searches for VWs of the prior ultrasound images acquired during prior ultrasound exams to identify a resultant ultrasound image that has the same VW as the current ultrasound image. The prior ultrasound exam may represent at least one ultrasound exam prior to the current ultrasound exam.

Additionally or alternatively, the medical imaging system may not identify the prior ultrasound image that has the VW that matches the current ultrasound image. The medical imaging system may increase a number of prior ultrasound exams used to find the matching VW. For example, the medical imaging system may increase a number of prior ultrasound exams to include earlier ultrasound exams.

The medical imaging system can identify the VWs of the current and prior ultrasound images based on a trained machine learning algorithm, which automatically classifies the VW. Optionally, the medical imaging system is configured to identify tags of the prior ultrasound images. The tags are indicative of one or more ultrasound image features, the VW, one or more anatomical features, the ultrasound exam type, and/or the like. The medical imaging system utilizes the tags to select a portion of the prior ultrasound images that match the current ultrasound image.

A technical effect of at least one embodiment described herein reduces a current ultrasound exam time. A technical effect of at least one embodiment described herein improves a clinical diagnosis or reduces a risk of a misdiagnosis of the clinician. A technical effect of at least one embodiment described herein increases a flexibility of the clinician to compare consecutive ultrasound exams.

Terms

The term "view window" for an ultrasound image refers to a view position, direction and/or orientation of the ultrasound image as captured by an ultrasound probe. Non-limiting examples of view windows (VW) include the parasternal view (e.g., long axis view, short axis view), apical view (e.g., 2 chamber view, 3 chamber view, 4 chamber view, 5 chamber view), and subcostal views (e.g., 4 chamber view, short axis view, inferior vena cava view). Ultrasound images with different view windows can be captured for a particular anatomical structure by adjusting the position, directional alignment and orientation of the ultrasound probe, which similarly adjusts the position, directional alignment and orientation of the field of view for the transducer(s) of the ultrasound probe.

The term "ultrasound exam" refers to an acquisition of one or more ultrasound images of one or more anatomical structures. The ultrasound exam can represent a continuous and/or discontinuous acquisition of the one or more ultrasound images (e.g., 2D, 3D, 4D) during a scan of a patient. The scan of the patient may last up to a minute and/or an hour. Optionally, the ultrasound exam can be based on one or more protocols.

The term "anatomical structure" refers to an anatomical part of a patient. Non-limiting examples of an anatomical structure include an organ (e.g., heart, kidney, lung, liver, bladder, brain, neonatal brain, embryo, abdomen, and/or the like), vascular structure (e.g., vein, artery, mitral valve, aortic valve, tricuspid valve, pulmonary valve), tissue or portion of an organ (e.g., breast tissue, liver tissue, brain tissue, cardiac tissue, prostate tissue, and/or the like), skeletal structure, and/or the like.

The term "anatomical feature" refers to a structural feature of the anatomical structure. Non-limiting examples of anatomical features include dimensions (e.g., height, length, width, depth), a shape, a boundary dimension (e.g., thickness, shape), a number of cavities or chambers, fiducial markers, and/or the like.

The term "anatomical measurement" refers to a measurement of the anatomical feature and/or the anatomical structure shown in an ultrasound image. The anatomical measurement may represent a volume, an area, a surface area, a wall thickness, a dimension, a blood flow, and/or the like.

The term "characteristic vector" refers to a list of one or more pixel characteristics that describe a pixel within an ultrasound image. The characteristic vector can include values for one or more of an intensity, a color, a gradient, and/or the like of the pixel.

The term "ultrasound image feature" refers to a presentation of the anatomical structure displayed within an ultrasound image. Non-limiting examples of the ultrasound image feature includes anatomical measurement graphics (e.g., overlaid measurements, cursors, visualizations), ultrasound image mode (e.g., Doppler, colorflow, B-mode), an anatomical feature, view window, noise of the ultrasound image, acquisition settings, and/or the like.

The term "real time" or "real-time" is used to refer to an operation, action or process performed by the medical imaging system (e.g., a controller circuit) during an ultrasound exam. An ultrasound exam may include collection of multiple separate 2D or 3D ultrasound images for a common or different view windows. Optionally, the ultrasound exam may include collection of one or more cine loops of 2D or 3D ultrasound data. The operation, action or process may be performed while actively scanning a patient and/or between separate scanning operations that occur during a single ultrasound exam. A length of time associated with real time may vary based on a processing speed and/or operating specification (e.g., no intentional lag or delay). Real time includes updating an ultrasound image shown on the display after each ultrasound pulse within a scan and/or after each ultrasound scan sequence. Additionally or alternatively, ultrasound data may be stored temporarily in memory of the medical imaging system during the ultrasound exam and processed in a live or off-line operation.

The term "machine learning algorithm" refers to an artificial intelligence algorithm that learns from various automatic or manual inputs, such as observations and/or data. The machine learning algorithm is adjusted over multiple iterations based on the as observations and/or data. For example, the machine learning algorithm is adjusted by supervised learning, unsupervised learning, and/or reinforcement learning. Non-limiting examples of machine learning algorithms are a decision tree, K-means, deep learning, artificial neural network, and/or the like.

The term "image analysis algorithm" refers to a machine learning algorithm that has been trained to perform image analysis to identify an ultrasound image feature (e.g., anatomical structure, anatomical features, a view window) in an ultrasound image.

The term "trend" refers to a change in a pathology of interest, an anatomical measurement, or anatomical function between a current ultrasound exam and a prior ultrasound exam. The trend is indicative of a change in the anatomical structure or function, where the change is associated with the pathology of interest and/or a change in the anatomical measurement. Non-limiting examples of trends represent a change in blood flow, dimensions of the anatomical structure or the anatomical characteristic, and/or the like.

The term "pathology of interest" refers to a portion of the anatomical structure having an irregular and/or structural deviation relative to a healthy anatomical structure. The pathology of interest represents the portion of the anatomical structure having a disease or illness. The pathology of interest may correspond to the portion of the anatomical structure having valvular stenosis, valvular insufficiency, valve regurgitation, arthritis, kidney stones, cancer, an obstruction, fetal abnormalities, and/or the like.

Figure 1:
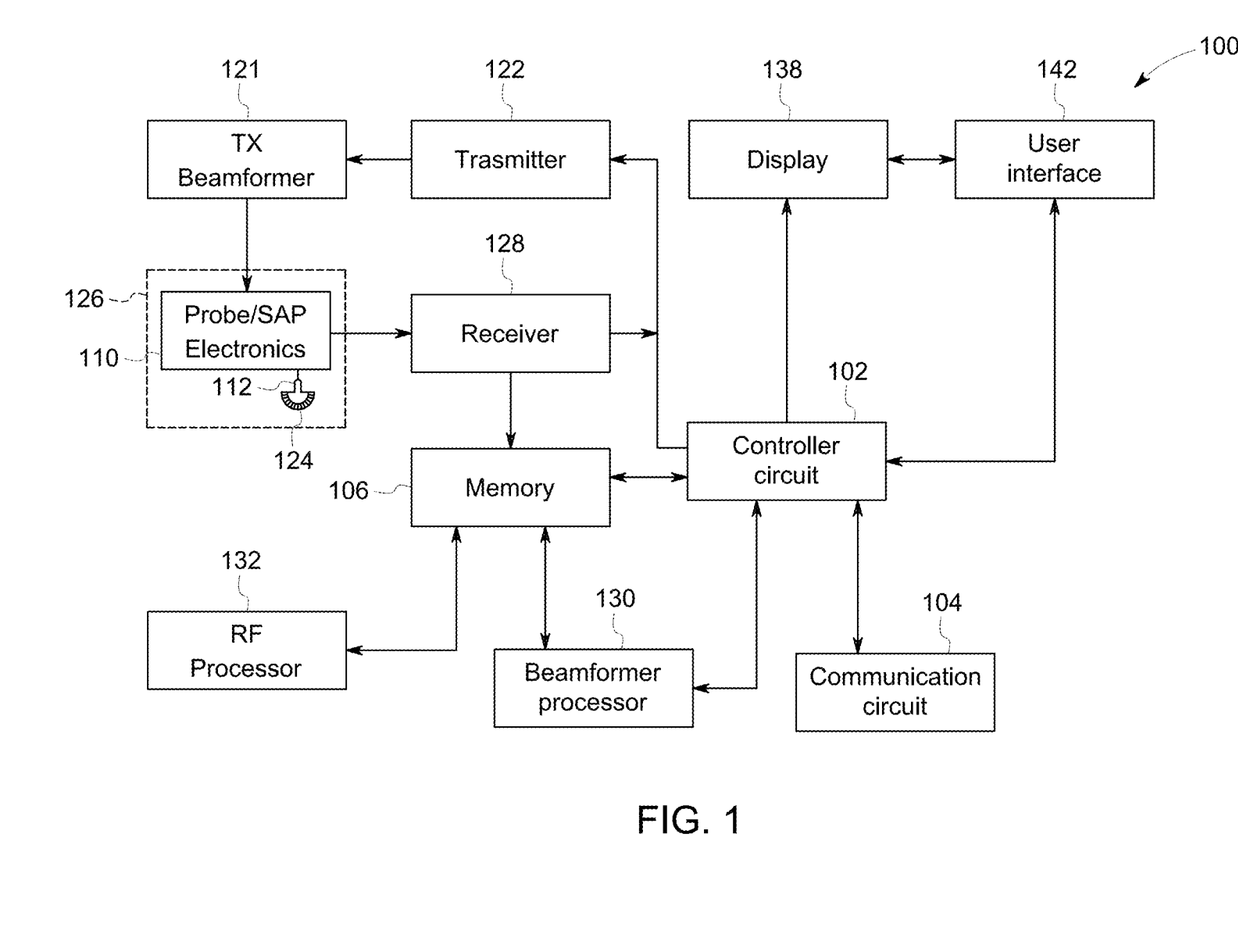
FIG. 1 illustrates a schematic block diagram of an embodiment of a medical imaging system.

FIG. 1 illustrates a schematic block diagram of an embodiment of a medical imaging system 100. For example, the medical imaging system 100 is shown as an ultrasound imaging system. The medical imaging system 100 may include a controller circuit 102 operably coupled to a communication circuit 104, a display 138, a user interface 142, an ultrasound probe 126, and a memory 106.

The controller circuit 102 is configured to control the operation of the medical imaging system 100. The controller circuit 102 may include one or more processors. Optionally, the controller circuit 102 may include a central processing unit (CPU), one or more microprocessors, a graphics processing unit (GPU), or any other electronic component capable of processing inputted data according to specific logical instructions. Optionally, the controller circuit 102 may include and/or represent one or more hardware circuits or circuitry that include, are connected with, or that both include and are connected with one or more processors, controllers, and/or other hardware logic-based devices. Additionally or alternatively, the controller circuit 102 may execute instructions stored on a tangible and non-transitory computer readable medium (e.g., the memory 106).

The controller circuit 102 is configured to identify an ultrasound image feature in a current ultrasound image. The ultrasound image feature may represent anatomical measurement graphics, the view window, the anatomical structure, ultrasound image mode, anatomical feature, and/or the like. The anatomical measurement graphics are indicative of anatomical measurements that were performed by the clinician on the ultrasound image. The current ultrasound image can be acquired during a current ultrasound exam in real time. Optionally, the current ultrasound image may be accessed by the controller circuit 102 in the memory 106. The ultrasound image feature may be identified by the controller circuit 102. For example, the controller circuit 102 may identify a view window (VW) of the current ultrasound image based on a position of the anatomical feature within the current ultrasound image. Based on the position of the anatomical feature and/or in relation to alternative anatomical features, the controller circuit 102 determines the VW of the current ultrasound image.

For example, the controller circuit 102 identifies six anatomical features within the current ultrasound image. The controller circuit 102 determines a size of a first anatomical feature relative to the alternative anatomical features within the current ultrasound image. Based on a size and position of the first anatomical feature, the controller circuit 102 determines a class or type of the first anatomical feature. For example, the controller circuit 102 determines that the first anatomical feature represents the left ventricle. The left ventricle is centrally located within the current ultrasound image and above a second anatomical feature. The controller circuit 102 determines the second anatomical feature is a left atrium separated by a mitral valve (e.g., a third anatomical feature). The controller circuit 102 identifies fourth, fifth, and sixth anatomical features positioned laterally with respect to the first, second, and third anatomical features. The controller circuit 102 determines the fourth anatomical feature is a right ventricle, and the sixth anatomical feature is a right atrium. The fifth anatomical feature is interposed between the fourth and sixth anatomical feature. The controller circuit 102 determines that the fifth anatomical feature is a tricuspid valve. Based on the positions of the anatomical features, the controller circuit 102 identifies the VW of the current ultrasound image as a four chamber apical view.

Additionally or alternatively, the controller circuit 102 is configured to identify other ultrasound image features of the current ultrasound image. For example, the controller circuit 102 can identify an ultrasound image mode (e.g., Doppler, B-mode, M-mode, C-mode), a depth of the scan, the noise of the image (e.g., speckle noise), the anatomical measurements shown in the current ultrasound image, the frequency of the ultrasound pulses emitted by the ultrasound probe 126, and/or the like.

The controller circuit 102 accesses a plurality of prior ultrasound images to find a resultant ultrasound image that includes the ultrasound image features of the current ultrasound image. The prior ultrasound images are acquired during a prior ultrasound exam. The prior ultrasound exam may represent one or more ultrasound exams performed on the same patient during preceding ultrasound exams. Additionally or alternatively, the prior ultrasound exam may represent more than one ultrasound exam, performed upon a population of one or more patients, preceding the current ultrasound exam. Optionally, the prior ultrasound images may include tags. The tags may be indicative of one or more ultrasound image features, such as the VW, one or more anatomical measurement graphics, the ultrasound image mode, the anatomical feature, noise of the ultrasound image, acquisition settings, and/or the like. Non-limiting examples of types of ultrasound exams are transthoracic echocardiogram, transrectal, transabdominal, transesophageal echocardiography, stress exams, and/or the like. The controller circuit 102 can select a set of the prior ultrasound images that include tags that are indicative of the ultrasound image features (e.g., the anatomical structure or features of the current ultrasound exam). The set of ultrasound images may be analyzed by the controller circuit 102 to identify the resultant ultrasound image.

For example, the controller circuit 102 compares the one or more anatomical features of the current ultrasound image with related anatomical features of the prior ultrasound images to identify the VW. For example, the controller circuit 102 identifies related anatomical features of the prior ultrasound images. For example, the controller circuit 102 analyzes the prior ultrasound images for anatomical features that indicate that the ultrasound image represents a left ventricle, a left atrium, a right ventricle, a right atrium, a mitral valve, or a tricuspid valve. For example, the anatomical features may indicate that the ultrasound image represents a four chamber view of the heart. Optionally, the anatomical feature may indicate that the ultrasound image represents a right ventricle. The controller circuit 102 identifies prior ultrasound images, that include the related anatomical features, as candidate ultrasound images. For example, the candidate ultrasound images may include all or a group of ultrasound images that are views of the right ventricle. Optionally, the candidate ultrasound images may be selected as the "best" matches to the current ultrasound image.

Additionally or alternatively, the controller circuit 102 is configured to compare additional ultrasound image features of the current ultrasound image with the prior ultrasound images. For example, the controller circuit 102 selects a portion of the prior ultrasound images that were acquired with the same ultrasound image mode as the current ultrasound image. In another example, the controller circuit 102 selects a portion of the prior ultrasound images that were acquired at the same depth and/or the same acquisition settings as the current ultrasound exam.

The controller circuit 102 is configured to determine the VW of the ultrasound image features of the candidate ultrasound images. The controller circuit 102 determines a position and/or orientation of the related anatomical features of the candidate ultrasound images. The position and/or orientation of the related anatomical features with respect to each other is indicative of the VW for the candidate ultrasound images. For example, the controller circuit 102 analyzes the position and/or orientation of anatomical features to determine the VW of the candidate ultrasound images (e.g., a left ventricle, a left atrium, a right ventricle, a right atrium, a mitral valve, or a tricuspid valve). For example, the anatomical features may indicate that the ultrasound image represents a four chamber apical view of the heart. Optionally, the anatomical feature may indicate that the ultrasound image represents a long axis parasternal view of the right ventricle. The controller circuit 102 compares a position and/or orientation of the one or more anatomical features to one another and/or to one or more reference points. The controller circuit 102 identifies a resultant ultrasound image from the candidate ultrasound images based on the related anatomical features having a common position and/or orientation as the one or more anatomical features of the current ultrasound image. For example, the controller circuit 102 identifies a resultant ultrasound image that has the same VW (e.g., 4-chamber apical view of the heart) as the current ultrasound image. Optionally, the controller circuit 102 identifies the resultant ultrasound image that matches additional ultrasound image features of the current ultrasound image.

The controller circuit 102 may display the resultant and current ultrasound image concurrently on the display 138. For example, the controller circuit 102 may display the resultant and current ultrasound image side-by-side.

The controller circuit 102 may be operably coupled to and/or control a communication circuit 104. The communication circuit 104 is configured to receive and/or transmit information with one or more alternative medical imaging systems, a remote server, and/or the like along a uni-directional and/or bi-directional communication link. The remote server may represent a database that includes patient information, machine learning algorithms, remotely stored ultrasound images (e.g., the prior ultrasound images) from prior ultrasound exams of a patient, and/or the like. The communication circuit 104 may represent hardware that is used to transmit and/or receive data along the uni-directional and/or bi-directional communication link. The communication circuit 104 may include a transceiver, receiver, transceiver and/or the like and associated circuitry (e.g., antennas) for wired and/or wirelessly communicating (e.g., transmitting and/or receiving) with the one or more alternative medical imaging systems, the remote server, and/or the like. For example, protocol firmware for transmitting and/or receiving data along the uni-directional and/or bi-directional communication link may be stored in the memory 106, which is accessed by the controller circuit 102. The protocol firmware provides the network protocol syntax for the controller circuit 102 to assemble data packets, establish and/or partition data received along the bi-directional communication links, and/or the like.

The uni-directional and/or bi-directional communication links may be a wired (e.g., via a physical conductor) and/or wireless communication (e.g., utilizing radio frequency (RF)) link for exchanging data (e.g., data packets) between the one or more alternative medical imaging systems, the remote server, and/or the like. The bi-directional communication links may be based on a customized communication protocol and/or a standard communication protocol, such as Ethernet, TCP/IP, Wi-Fi, 802.11, Bluetooth, and/or the like.

The controller circuit 102 is operably coupled to the display 138 and the user interface 142. The display 138 may include one or more liquid crystal displays (e.g., light emitting diode (LED) backlight), organic light emitting diode (OLED) displays, plasma displays, CRT displays, and/or the like. The display 138 may display patient information, one or more ultrasound images and/or videos, components of a graphical user interface, one or more 2D, 3D, or 4D ultrasound image data sets from ultrasound data stored in the memory 106 or currently being acquired in real-time, anatomical measurements, diagnosis, treatment information, tags, and/or the like received by the display 138 from the controller circuit 102.

The user interface 142 controls operations of the controller circuit 102 and the medical imaging system 100. The user interface 142 is configured to receive inputs from the clinician and/or operator of the medical imaging system 100. The user interface 142 may include a keyboard, a mouse, a touchpad, one or more physical buttons, and/or the like. Optionally, the display 138 may be a touch screen display, which includes at least a portion of the user interface 142. For example, a portion of the user interface 142 may correspond to a graphical user interface (GUI) generated by the controller circuit 102, which is shown on the display 138. The touch screen display can detect a presence of a touch from the operator on the display 138 and can also identify a location of the touch with respect to a surface area of the display 138. For example, the user may select one or more user interface components of the GUI shown on the display by touching or making contact with the display 138. The user interface components may correspond to graphical icons, textual boxes, menu bars, and/or the like shown on the display 138. The user interface components may be selected, manipulated, utilized, interacted with, and/or the like by the clinician to instruct the controller circuit 102 to perform one or more operations as described herein. The touch may be applied by, for example, at least one of an individual's hand, glove, stylus, and/or the like.

The memory 106 includes parameters, algorithms, protocols of one or more ultrasound exams, data values, and/or the like utilized by the controller circuit 102 to perform one or more operations described herein. The memory 106 may be a tangible and non-transitory computer readable medium such as flash memory, RAM, ROM, EEPROM, and/or the like.

The memory 106 may include an image analysis algorithm. The controller circuit 102 executes the image analysis algorithm to identify the anatomical features in the ultrasound image, and the VW of the anatomical structure. Optionally, the image analysis algorithm may be received along one of the bi-directional communication links via the communication circuit 104 and stored in the memory 106.

The image analysis algorithm may be defined by one or more machine learning algorithms to identify the anatomical structure in the ultrasound image based on the anatomical feature. Additionally or alternatively, the image analysis algorithm is configured to determine a view window (VW) of the anatomical structure. The image analysis algorithm may be executed by the controller circuit 102 as the ultrasound images are being acquired (e.g., in real-time) by the medical imaging system 100. Additionally or alternatively, the image analysis algorithm may be executed by the controller circuit 102 as the ultrasound images are loaded by the clinician from the memory 106.

Optionally, the image analysis algorithm utilizes a pixel and/or voxel analysis of the ultrasound image. For example, the anatomical feature is identified by the controller circuit 102 based on characteristics of the pixels and/or voxels in the ultrasound image. The controller circuit 102 defines characteristic vectors for the pixels and/or voxels. The characteristic vector may represent an array of information that describes the pixels and/or voxels. The characteristic vector includes gradients, a color, an intensity or brightness, and/or the like of the pixels and/or voxels. Optionally, the image analysis algorithm may correspond to an artificial neural network formed by the controller circuit 102 and/or the remote server. The image analysis algorithm may be divided into a plurality of artificial neural layers. The artificial neural layers may represent different functions and/or outputs of the image analysis algorithm. For example, the artificial neural layers include an input layer configured to receive an input image, an output layer configured to identify the anatomical structure of the input image, a VW layer, and/or one or more intermediate layers. The artificial neural layers represent different groups or sets of artificial neurons, which can represent different functions performed by the controller circuit 102 on the ultrasound image. The artificial neurons in the layers are configured to examine individual pixels in the ultrasound image. For example, the artificial neurons may define the characteristic vectors for the ultrasound image.

The artificial neurons further may apply different weights in the functions applied to the ultrasound image to attempt to identify the anatomical structure. The image analysis algorithm identifies the anatomical structure by assigning or associating different pixels in the ultrasound image with different anatomical features based on the characteristic vectors. For example, the characteristics vectors are utilized by the controller circuit 102 to determine scores for the pixels. The scores can indicate the probability that the pixel represents a particular anatomical feature.

Additionally or alternatively, the image analysis algorithm uses a classification or object based algorithm to identify the anatomical feature. For example, the classification algorithm identifies one or more anatomical features in the ultrasound image. The identification of the one or more anatomical features can be based on a size, a shape, and/or the like. The classification algorithm classifies (e.g., random forest classifier, principal component analysis, and/or that like) the one or more anatomical features into a plurality of categories or classes. The categories or classes represent different anatomical feature of anatomical structures. Non-limiting examples are chambers, valves, cellular structure, and/or the like The controller circuit 102 may determine the VW of the anatomical structure based on one or more of the anatomical features. For example, controller circuit 102 identifies an orientation and/or spatial position of the one or more anatomical features within the ultrasound image. The controller circuit 102 determines the VW based on the orientation and/or spatial position of the one or more anatomical features with respect to each other. The spatial position may include a distance(s) and/or relation between at least two of the anatomical features. Change in the spacing between at least two anatomical features may occur when the anatomical structure is not perpendicular to the VW of the transducer array 112.

Additionally or alternatively, the image analysis algorithm is configured to identify one or more of the anatomical features independent of the ultrasound image mode. For example, the image analysis algorithm is configured to identify one or more of the anatomical features of a color flow ultrasound image, a B-mode ultrasound image, a C-mode ultrasound image, an M-mode ultrasound image, and/or the like.

The ultrasound probe 126 may have a transmitter 122, transmit beamformer 121 and probe/SAP electronics 110. The probe/SAP electronics 110 may be used to control the switching of the transducer elements 124. The probe/SAP electronics 110 may also be used to group transducer elements 124 into one or more sub-apertures. The ultrasound probe 126 may be configured to acquire ultrasound data or information from the anatomical structure of the patient. The ultrasound probe 126 is communicatively coupled to the controller circuit 102 via the transmitter 122. The transmitter 122 transmits a signal to a transmit beamformer 121 based on acquisition settings received by the controller circuit 102. The acquisition settings may define an amplitude, pulse width, frequency, gain setting, scan angle, power, time gain compensation (TGC), resolution, and/or the like of the ultrasonic pulses emitted by the transducer elements 124. The transducer elements 124 emit pulsed ultrasonic signals into the patient (e.g., a body). The acquisition settings may be defined by the user operating the user interface 142. The signal transmitted by the transmitter 122 in turn drives a plurality of transducer elements 124 within a transducer array 112.

The transducer elements 124 emit pulsed ultrasonic signals into a body (e.g., patient) or volume corresponding to the acquisition settings along one or more scan planes. The ultrasonic signals may include, for example, one or more reference pulses, imaging pulses, one or more pushing pulses (e.g., shear-waves), and/or one or more pulsed wave Doppler pulses. At least a portion of the pulsed ultrasonic signals backscatter from the anatomical structure to produce echoes. The echoes are delayed in time and/or frequency according to a depth or movement, and are received by the transducer elements 124 within the transducer array 112. The ultrasonic signals may be used for imaging, for generating and/or tracking shear-waves, for measuring changes in position or velocity within the anatomic structure, differences in compression displacement of the tissue (e.g., strain), and/or for therapy, among other uses. For example, the probe 126 may deliver low energy pulses during imaging and tracking, medium to high energy pulses to generate shear-waves, and high energy pulses during therapy.

The transducer elements 124 convert the received echo signals into electrical signals, which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored in memory 106, temporarily. The digitized signals correspond to the backscattered waves received by each transducer element 124 at various times. After digitization, the signals still may preserve the amplitude, frequency, phase information of the backscatter waves.

Optionally, the controller circuit 102 may retrieve the digitized signals stored in the memory 106 to prepare for the beamformer processor 130. For example, the controller circuit 102 may convert the digitized signals to baseband signals or compressing the digitized signals.

The beamformer processor 130 may include one or more processors. Optionally, the beamformer processor 130 may include a central processing unit (CPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 106) for beamforming calculations using any suitable beamforming method such as adaptive beamforming, synthetic transmit focus, aberration correction, synthetic aperture, clutter reduction and/or adaptive noise control, and/or the like. Optionally, the beamformer processor 130 may be integrated with and/or a part of the controller circuit 102. For example, the operations described as being performed by the beamformer processor 130 may be configured to be performed by the controller circuit 102.

The beamformer processor 130 performs beamforming on the digitized signals of transducer elements and outputs a radio frequency (RF) signal. The RF signal is then provided to an RF processor 132 that processes the RF signal. The RF processor 132 may include one or more processors. Optionally, the RF processor 132 may include a central processing unit (CPU), one or more microprocessors, or any other electronic component capable of processing inputted data according to specific logical instructions. Additionally or alternatively, the RF processor 132 may execute instructions stored on a tangible and non-transitory computer readable medium (e.g., the memory 106). Optionally, the RF processor 132 may be integrated with and/or a part of the controller circuit 102. For example, the operations described as being performed by the RF processor 132 may be configured to be performed by the controller circuit 102.

The RF processor 132 may generate different ultrasound image data types and/or modes (e.g., B-mode, C-mode, M-mode, color Doppler (e.g., color flow, velocity/power/variance), tissue Doppler, and Doppler energy) for multiple scan planes or different scanning patterns based on the predetermined settings of the first model. For example, the RF processor 132 may generate tissue Doppler data for multi-scan planes. The RF processor 132 gathers the information (e.g., I/Q, B-mode, color Doppler, tissue Doppler, and Doppler energy information) related to multiple data slices and stores the data information, which may include time stamp and orientation/rotation information, in the memory 106.

Alternatively, the RF processor 132 may include a complex demodulator (not shown) that demodulates the RF signal to form IQ data pairs representative of the echo signals. The RF or IQ signal data may then be provided directly to the memory 106 for storage (e.g., temporary storage). Optionally, the output of the beamformer processor 130 may be passed directly to the controller circuit 102.

The controller circuit 102 may be configured to process the acquired ultrasound data (e.g., RF signal data or IQ data pairs) and prepare and/or generate frames of ultrasound image data representing the anatomical structure for display on the display 138. Acquired ultrasound data may be processed in real-time by the controller circuit 102 during the ultrasound exam as the echo signals are received. Additionally or alternatively, the ultrasound data may be stored temporarily in the memory 106 during the ultrasound exam and processed in less than real-time in a live or off-line operation.

The memory 106 may be used for storing processed frames of acquired ultrasound data that are not scheduled to be displayed immediately or to store post-processed images, firmware or software corresponding to, for example, a graphical user interface, one or more default image display settings, programmed instructions, and/or the like. The memory 106 may store the ultrasound images such as 3D ultrasound image data sets of the ultrasound data, where such 3D ultrasound image data sets are accessed to present 2D and 3D images. For example, a 3D ultrasound image data set may be mapped into the corresponding memory 106, as well as one or more reference planes. The processing of the ultrasound data, including the ultrasound image data sets, may be based in part on user inputs, for example, user selections received at the user interface 142.

Figure 2:
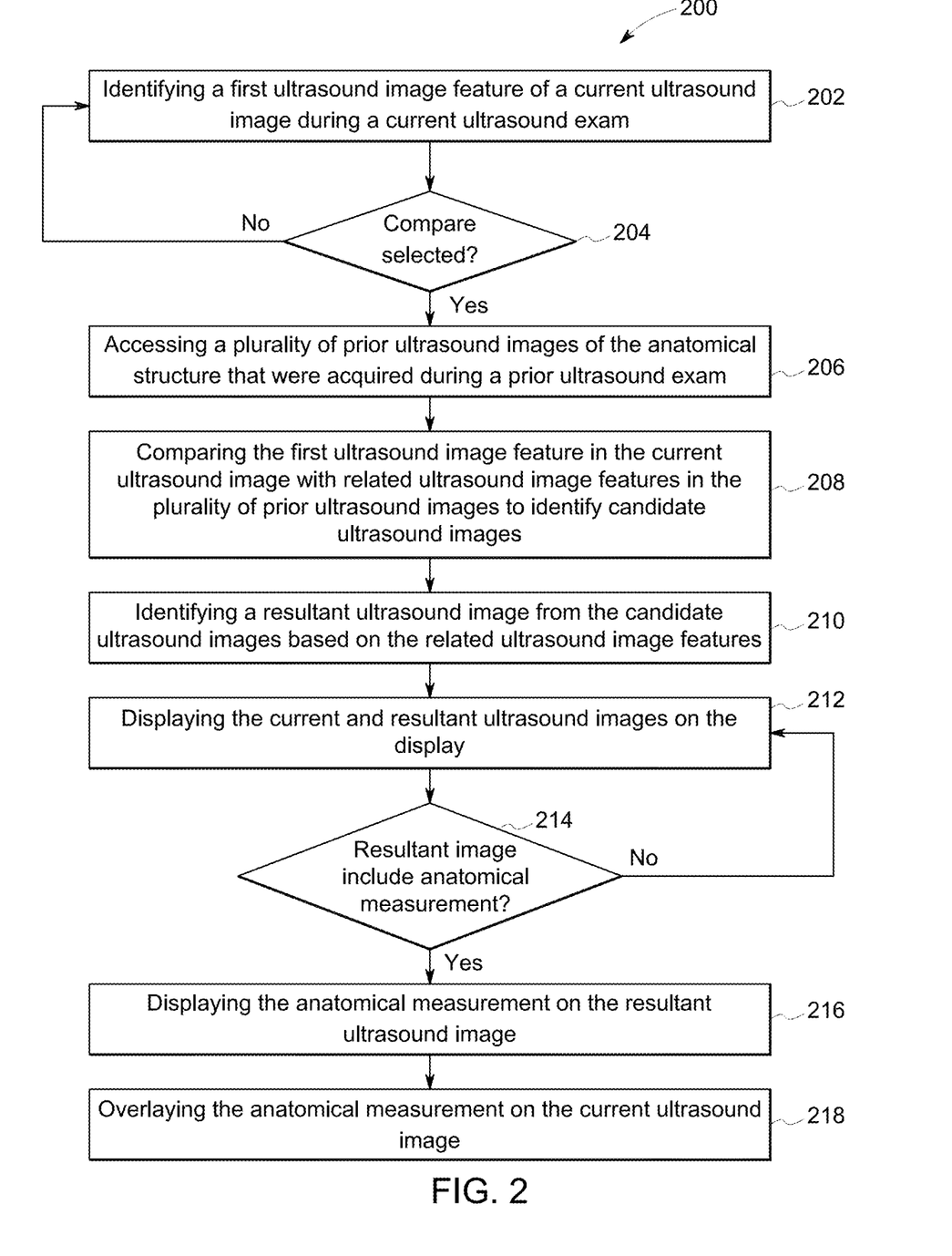
FIG. 2 illustrates a flow chart of an embodiment of a method for identifying an ultrasound image between ultrasound exams.

FIG. 2 illustrates a flow chart of an embodiment of a method 200 for grouping a plurality of ultrasound images acquired during an ultrasound exam, in accordance with embodiments herein. The method 200, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It may be noted that the steps described of the method 200 may be performed during the ultrasound exam in real-time. In various embodiments, portions, aspects, and/or variations of the method 200 may be used as one or more algorithms to direct hardware to perform one or more operations described herein.

Figure 3:
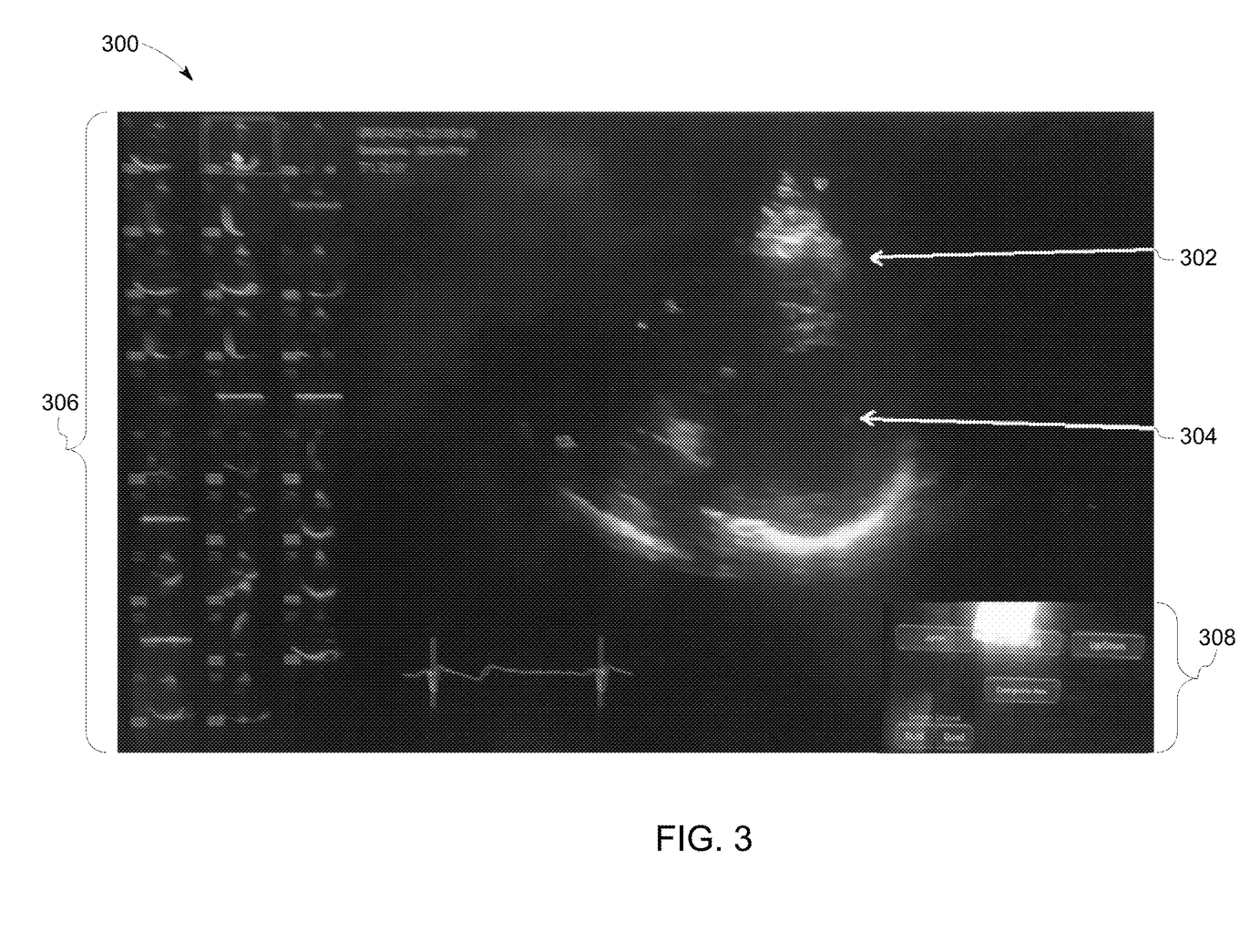
FIG. 3 illustrates a graphical user interface of a current ultrasound image during a current ultrasound exam, according to an embodiment.

Beginning at 202, the controller circuit 102 identifies a first ultrasound image feature of a current ultrasound image 302 during a current ultrasound exam. FIG. 3 illustrates a graphical user interface (GUI) 300 of the current ultrasound image 302 during a current ultrasound exam, according to an embodiment. The current ultrasound image 302 is based on ultrasound data received from the ultrasound probe 126. The ultrasound probe 126 acquires ultrasound data of the anatomical structure within the patient. During the current ultrasound exam of the patient, the ultrasound probe 126 may emit ultrasound signals from the transducer array 112 at a set rate within the patient. At least a portion of the ultrasound signals are backscattered from the anatomical structure of interest and received by the ultrasound probe 126 via the receiver 128 as ultrasound data. The controller circuit 102 is configured to generate the plurality of ultrasound images of the anatomical structure based on the ultrasound data. The controller circuit 102 may be configured to process the acquired ultrasound data (e.g., RF signal data or IQ data pairs) from the ultrasound probe 126 and prepare and/or generate frames of ultrasound image data. The ultrasound image data represent a plurality of ultrasound images 306 of the anatomical structure acquired during the current ultrasound exam.

Additionally or alternatively, the clinician may select the current ultrasound image from the plurality of ultrasound images 306 stored in the memory 106. For example, the plurality of ultrasound images 306 were acquired during the current ultrasound exam. The clinician can select one of the plurality of ultrasound images 306 for the current ultrasound image 302 using the user interface 142. For example, the controller circuit 102 receives a user selection from the user interface 142 selecting the current ultrasound image 302.

The controller circuit 102 analyzes the current ultrasound image 302 to identify a first ultrasound image feature. For example, the controller circuit 102 may identify a view window of the current ultrasound image 302. For example, the controller circuit 102 executes the image analysis algorithm stored in the memory 106. The controller circuit 102 identifies a first anatomical feature 304. For example, the controller circuit 102 determines a first set of characteristic vectors for the current ultrasound images 302. The sets of characteristic vectors includes one or more components representing the pixels of the current ultrasound image 302. For example, the one or more components can represent an intensity, a color, a gradient, and/or the like representing the pixels. The controller circuit 102 generate histograms for the one or more components of the characteristic vectors. The controller circuit 102 may group one or more components that have intensities, colors, gradients, and/or the like similar to each other. For example, the controller circuit 102 groups the pixels that have one or more components that are within a predetermined component threshold. The controller circuit 102 generates histograms for the groups of pixels. The histograms may represent one or more components of the pixels within common groups. The controller circuit 102 compares the histograms to identify the anatomical feature 304 of the current ultrasound image 302.

For example, the controller circuit 102 compares the histograms with trained histograms of anatomical features of the image analysis algorithm. The controller circuit 102 determines probabilities that the groups of pixels represent one of the anatomical features. The probabilities representing an identity of the first anatomical feature 304. The probabilities can be represented as one or more vectors. The one or more vectors [a b c d] may be associated with probabilities that the pixel represents various different anatomical features, where the values of a, b, c, and d indicate the probability of the pixel representing each of a different classes or types of anatomical features. The controller circuit 102 identifies the first anatomical feature 304 as the left atrium. For example, the controller circuit 102 identifies the first anatomical feature 304 having a higher probability of being the left atrium relative to the remaining probabilities. Additionally or alternatively, the controller circuit 102 can classify the first anatomical feature 304 based on a size, shape, and/or the like. The controller circuit 102 determines the VW of the current ultrasound image 302. The controller circuit 102 determines the VW based on the orientation and/or spatial position of the first anatomical feature 304 within the current ultrasound image 302 and/or relative to alternative anatomical features.

The controller circuit 102 may identify one or more of the anatomical features of the plurality of ultrasound images 306 concurrently and/or simultaneously. For example, the controller circuit 102 analyzes the plurality of ultrasound images 306 concurrently, simultaneously, and/or in real-time.

Additionally or alternatively, the controller circuit 102 identifies other ultrasound image features of the current ultrasound image 302. For example, the controller circuit 102 receives a selection from the user interface 142 for the ultrasound image mode, such as the B-mode as shown in FIG. 3, as the ultrasound image feature of the current ultrasound image 302. The ultrasound image mode is based on the ultrasound image data type generated by the RF processor 132 and stored in the memory 106. The controller circuit 102 identifies the ultrasound image data type stored in the memory 106 to determine the ultrasound image mode.

In another example, the controller circuit 102 receives acquisition settings representing the ultrasound image features. The controller circuit 102 identifies the acquisition settings for the current ultrasound image 302. The acquisition settings of the current ultrasound image 302 is stored in the memory 106. The acquisition settings may define an amplitude, pulse width, frequency, gain setting, scan angle, power, TGC, resolution, and/or the like of the ultrasonic pulses emitted by the transducer elements 124.

In another example, the controller circuit 102 identifies the noise of the current ultrasound image 302 representing the ultrasound image feature. The controller circuit 102 determines the noise of the current ultrasound image 302. The noise of the current ultrasound image 302 can be determined by the controller circuit 102. For example, the controller circuit 102 utilizes a K-distribution relative to the frequency of the ultrasonic pulses.

In another example, the controller circuit 102 identifies anatomical measurements performed on the current ultrasound image 302 representing the ultrasound image feature. For example, the controller circuit 102 receives anatomical measurements from the user interface 142. The controller circuit 102 overlays the anatomical measurements on the current ultrasound image 302, and identifies the anatomical measurements. For example, the controller circuit 102 identifies a position of one or more cursors, a length measurement, an area measurement, and/or the like.

At 204, the controller circuit 102 determines whether a compare operation is selected. The compare operation indicates that the controller circuit 102 identifies a prior ultrasound image that includes the first ultrasound image feature as the current ultrasound image 302. The GUI 300 includes a plurality of user interface component 308. The clinician can select one or more of the user interface components 308 to adjust operations of the medical imaging system 100. For example, the selection of one or more of the user interface components 308 instruct the controller circuit 102 to adjust ultrasound signals transmitted by the ultrasound probe 126, selection of different ultrasound imaging modes, one or more anatomical measurements, compare the current ultrasound image 302 with prior ultrasound exams, and/or the like based on selections of the user interface components 308.

The clinician may select one of the interface components 308 from the user interface 142 to compare the current ultrasound image 302 with prior ultrasound exams. The controller circuit 102 receives the selection from the user interface 142, and determines that the compare operation is selected.

If the compare operation is selected, then at 206, the controller circuit 102 accesses a plurality of prior ultrasound images that were acquired during one or more prior ultrasound exams. The prior ultrasound images may be stored in the memory 106. Additionally or alternatively, the controller circuit 102 may receive the plurality of prior ultrasound images along the uni-directional or bi-directional communication link from the remote server.

At 208, the controller circuit 102 compares the first ultrasound image feature in the current ultrasound image 302 with related ultrasound image features in the plurality of prior ultrasound images to identify candidate ultrasound images. The related ultrasound image features represent common ultrasound image features in the plurality of prior ultrasound images and the current ultrasound image 302.

For example, the controller circuit 102 identifies candidate ultrasound images that have the same VW as the current ultrasound image 302. The controller circuit 102 can identify the candidate ultrasound images based on sets of characteristic vectors of the prior ultrasound images. For example, the controller circuit 102 selects the candidate ultrasound images from the prior ultrasound images that have sets of characteristic vectors that are similar and/or match the first set of characteristic vector of the current ultrasound image 302.

For example, the controller circuit 102 executes the image analysis algorithm stored in the memory 106. The controller circuit 102 analyzes the prior ultrasound images to define sets of characteristic vectors. The sets of characteristic vectors includes the one or more components representing the pixels of the prior ultrasound images. The controller circuit 102 generate histograms for the one or more components of the sets of characteristic vectors. The controller circuit 102 may group one or more components of each of the prior ultrasound images that have intensities, colors, gradients, and/or the like similar to each other. For example, the controller circuit 102 groups the pixels that have one or more components that are within the predetermined component threshold. The groups represent the related anatomical features of the prior ultrasound images.

The controller circuit 102 generates histograms for the related anatomical features. The controller circuit 102 compares the histograms of the related anatomical features to the histogram of the anatomical feature 304. The controller circuit 102 identifies the prior ultrasound images that have related anatomical features that match the first anatomical feature 304 within a set threshold. For example, the controller circuit 102 compares a related histogram representing intensities of a related anatomical feature of a prior ultrasound image. The intensities are indicative of an overall shape of the related anatomical feature. The controller circuit 102 compares the related histogram with a histogram of intensities of the anatomical feature 304. The controller circuit 102 may compare a number of pixels having similar intensities. Additionally or alternatively, the controller circuit 102 generates histographs of the histograms and compares a morphology of the histographs with each other. The matching of histograms based on the first set and sets of characteristic vectors by the controller circuit 102 is indicative that the related anatomical features are in the same class (e.g., the left atrium), as the first anatomical feature 304.

Additionally or alternatively, the controller circuit 102 identifies the candidate ultrasound images based on the ultrasound image feature having a common ultrasound image mode as the current ultrasound image 302. The controller circuit 102 selects the plurality of prior ultrasound images that match the ultrasound image mode as the current ultrasound image 302. The selected prior ultrasound images are used by the controller circuit 102 to form the candidate ultrasound images.

In another example, the controller circuit 102 identifies the candidate ultrasound images based on the ultrasound image feature having a common anatomical measurements as the current ultrasound image 302. The controller circuit 102 identifies the anatomical measurements of the plurality of prior ultrasound images. For example, the controller circuit 102 identifies a type of anatomical measurement of the plurality of prior ultrasound images. The controller circuit 102 identifies a length anatomical measurement overlaid on the prior ultrasound images, position of cursors relative to the anatomical features of the prior ultrasound images, an area measurement of the anatomical features, and/or the like. The controller circuit 102 compares the anatomical measurements of the prior ultrasound images with the current ultrasound image 302. The controller circuit 102 may select the plurality of prior ultrasound images that have a common ultrasound image with the current ultrasound image 302 are selected as the candidate ultrasound images.

Additionally or alternatively, the controller circuit 102 may select a portion of the prior ultrasound images based on one or more tags. For example, at least a portion of the plurality of prior ultrasound images may include the tags. The tags are indicative of the ultrasound image feature, such as the VW, the anatomical measurement graphics, the anatomical feature, the noise of the prior ultrasound images, and/or the like. The tags may be generated by the controller circuit 102 executing the image analysis algorithm during the prior ultrasound exam and/or when selected by the clinician. For example, the controller circuit 102 identifies the tags of the plurality of prior ultrasound images. The controller circuit 102 selects a set of ultrasound images from the plurality of prior ultrasound images having the tags, that can be indicative of the first anatomical feature 304. For example, the controller circuit 102 may compare the tags of the prior ultrasound images with the first anatomical feature 304. The controller circuit 102 identifies tags that match the first anatomical feature 304 to form the set of ultrasound images. Additionally or alternatively, the tags may represent a VW of the prior ultrasound images. The controller circuit 102 identifies tags that match the current ultrasound image 302 to form the set of ultrasound images. The controller circuit 102 analyzes the set of ultrasound images for the related anatomical features. For example, the candidate ultrasound images are in the set of ultrasound images.

At 210, the controller circuit 102 identifies one or more resultant ultrasound images 404 (FIG. 4) from the candidate ultrasound image based on the related ultrasound image features.

Figure 4:
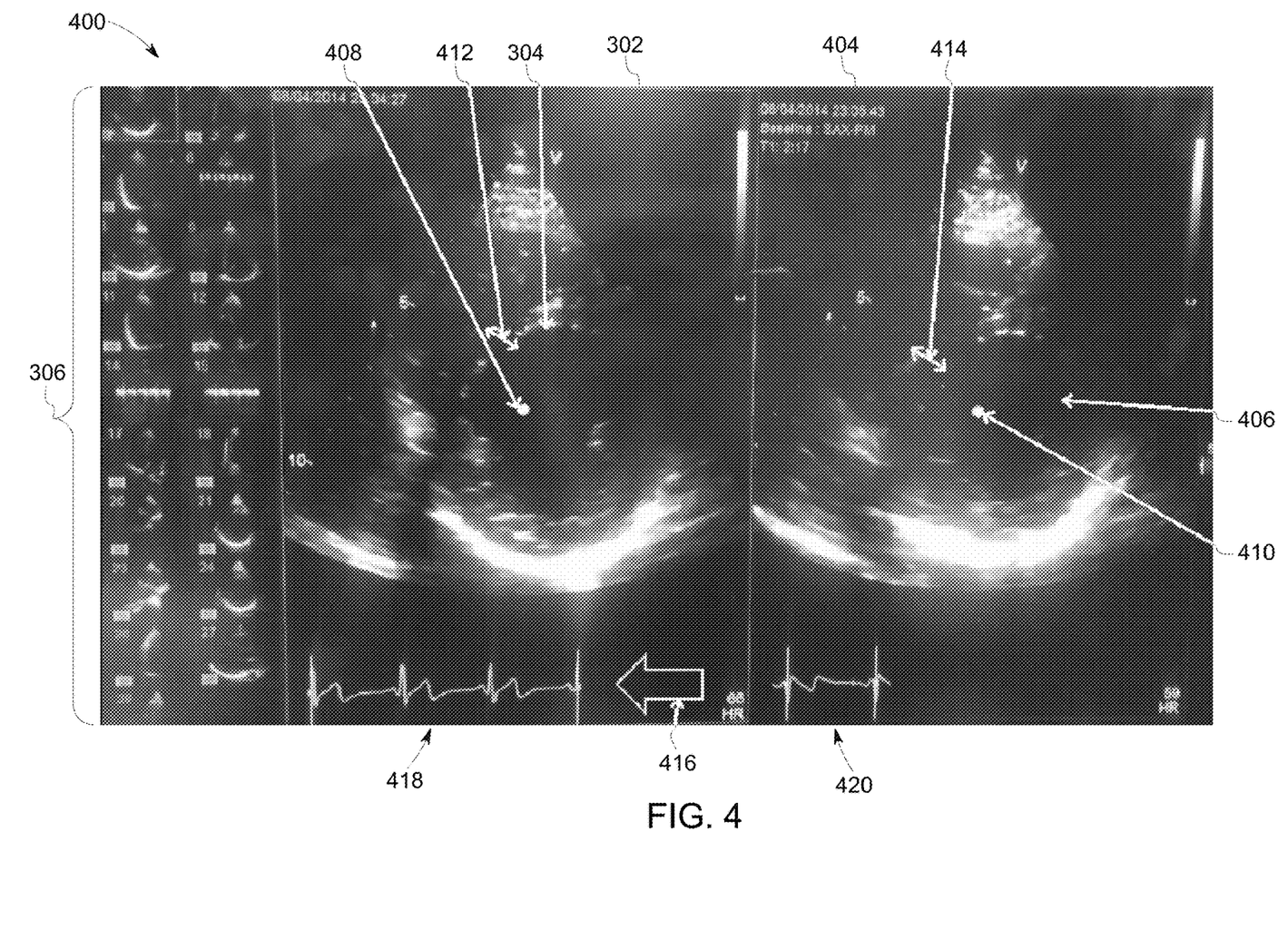
FIG. 4 illustrates a graphical user interface of current and resultant ultrasound images, according to an embodiment.

For example, the controller circuit 102 identifies the resultant ultrasound image 404 based on a common VW (e.g., ultrasound image feature). The controller circuit 102 identifies an anatomical feature of the resultant ultrasound image 404 having a common position as the first anatomical feature 304. The controller circuit 102 may identify the resultant ultrasound image 404 from the first set and sets of characteristic vectors. For example, the controller circuit 102 determines candidate differences between the sets of characteristic vectors with the first set of characteristic vectors. The candidate differences represent differences in color, intensity, gradient, and/or the like of the pixels between the current and candidate ultrasound images. The controller circuit 102 selects the resultant ultrasound image 404 having a candidate difference within a predetermined non-zero threshold of the first set of feature vectors. For example, the controller circuit 102 selects one of the candidate ultrasound images as the resultant ultrasound image 404 having a smallest candidate difference relative to the remaining candidate ultrasound images.

Concurrently and/or simultaneously, the controller circuit 102 compares a position of the first anatomical feature 304 relative to the current ultrasound image to a position of the related anatomical features of the candidate ultrasound images. In connection with FIG. 4, the controller circuit 102 may determine the positions of the first and related anatomical features 304, 406 based on reference points 408, 410, relative positions of the first and related anatomical features 304, 406, relative to alternative anatomical features, and/or the like.

FIG. 4 illustrates a GUI 400 of the current and resultant ultrasound images 302, 404, according to an embodiment. The controller circuit 102 identified the related anatomical feature 406 of the resultant ultrasound image 404. The controller circuit 102 may determine a common position of the first and related anatomical features 304, 406 based on a reference position of the current ultrasound image 302. For example, the controller circuit 102 may calculate a reference point 408. The reference point 408 may represent a center position of the current ultrasound image 302. The controller circuit 102 may determine a distance between a center of the first anatomical feature 304 and the reference point 408. The distance may be compared to a reference distance between a second reference point 410 and the related anatomical feature 406.

The second reference point 410 is determined by the controller circuit 102 at a center position of the resultant ultrasound image 404. The controller circuit 102 determines a reference distance between the second reference point 410 and a center of the related anatomical feature 406. The controller circuit 102 determines a difference between the reference distance and the distance. The difference is compared with a predetermined distance threshold stored in the memory 106. If the difference is less than the predetermined distance threshold, the controller circuit 102 determines the first and related anatomical features 304, 406 are in the common position.

Additionally or alternatively, the controller circuit 102 determines the common position relative to an alternative anatomical feature in the current and resultant ultrasound image 302, 404. For example, the controller circuit 102 determines a distance 412 between the anatomical feature 304 and an alternative anatomical feature in the current ultrasound image 302. The controller circuit 102 determines a reference distance 414 between the related anatomical feature 406 and the alternative anatomical feature in the resultant ultrasound image 404. The controller circuit 102 determines a difference between the distances 412, 414. The difference is compared with a predetermined distance threshold stored in the memory 106. If the difference is less than the predetermined distance threshold, the controller circuit 102 determines the first and related anatomical features 304, 406 are in the common position.

Additionally or alternatively, the controller circuit 102 may determine a common position of the first and related anatomical features 304, 406 based on a difference in positions of centers of the first and related anatomical features 304, 406. For example, the controller circuit 102 calculates a center of the first anatomical feature 304. The controller circuit 102 determines a coordinate (e.g., Cartesian coordinate) of the center relative to the current ultrasound image 302. For example, the coordinate can be relative to the reference point 408. The controller circuit 102 calculates a second center of the related anatomical features 406. The controller circuit 102 determines a coordinate of the center relative to the resultant ultrasound image 404. For example, the coordinate can be relative to the second reference point 410. The controller circuit 102 compares the coordinates of the first and related anatomical features 304, 406. For example, the controller circuit 102 determines a distance between the coordinates. If the distance is less than the predetermined distance threshold, the controller circuit 102 determines the first and related anatomical features 304, 406 are in the common position.

Optionally, the controller circuit 102 may compare additional information to identify the resultant ultrasound image 404. The additional information may include anatomical functions performed by the anatomical structure. Non-limiting examples of anatomical functions are a cardiovascular function (e.g., diastolic function, systolic function, cardiac cycle), a renal function, a digestive function, a metabolic function, a detoxification function, and/or the like. Cardiac information 418, 420 of the anatomical structure is included with the current and resultant ultrasound images 302, 404. The cardiac information 418, 420 is illustrated as an Electrocardiography waveform. The controller circuit 102 may compare the cardiac information 418 of the current ultrasound image 302 with the candidate ultrasound images. For example, the controller circuit 102 compares a morphology (e.g., slope, peak amplitude, peak position) of the cardiac information 418 with the cardiac information 420 of the candidate ultrasound images. The controller circuit 102 identifies a difference between the cardiac information 418, 420 of the current and the candidate ultrasound images that are within a pre-determined non-zero threshold of each other. Optionally, the controller circuit 102 may determine a heart rate based on the cardiac information 418, 420. For example, the controller circuit 102 calculates a length of a cardiac cycle to determine the heart rate from the cardiac information 418, 420.

Additionally or alternatively, the controller circuit 102 compares additional ultrasound image features to identify the resultant ultrasound image 404. For example, the controller circuit 102 calculates the noise of the candidate ultrasound images. The controller circuit 102 may select the resultant ultrasound image 404 from the candidate ultrasound images. For example, the controller circuit 102 determines that the noise of the resultant ultrasound image 404 matches the noise of the current ultrasound image 302 within a predetermined threshold such that the noise of the resultant ultrasound image 404 closer matches the current ultrasound image 302 relative to the remaining candidate ultrasound images.

Optionally, the controller circuit 102 identifies more than one resultant ultrasound image having common ultrasound image features with the current ultrasound image 302. For example, the controller circuit 102 identifies three resultant ultrasound images from three prior ultrasound exams, respectively. The controller circuit 102 concurrently displays the three resultant ultrasound images with the current ultrasound image 302. For example, the controller circuit 102 subdivides the display into four portions to display the current ultrasound image 302 and the three resultant images concurrently.

At 212, the controller circuit 102 displays the current and resultant ultrasound images 302, 404 on the display 138. For example, the GUI 400 displays the current and resultant ultrasound image 302, 404 concurrently on the display 138. The GUI 400 displays the current and resultant ultrasound image 302, 404 side by side. Additionally or alternatively, the current and resultant ultrasound image 302, 404 are displayed at different positions relative to each other (e.g., top and bottom, overlaid).

Optionally, the controller circuit 102 may display a graphical icon 416 on the display 138. The graphical icon 416 is indicative of an adjustment to the ultrasound probe 126 to decrease the candidate difference. The graphical icon 416 may is show as an arrow. The arrow representing the adjustment in position of the ultrasound probe 126. Optionally, the graphical icon 416 may be animated to illustrating an adjustment of the ultrasound probe 126. The adjustment is based on the first set of characteristics vectors and the set of characteristic vectors of the resultant ultrasound image 402. For example, the controller circuit 102 determines an adjustment in the VW of the ultrasound probe 126 to decrease the candidate difference. The adjustment determined by the controller circuit 102 further aligns the first set and the sets of characteristic vectors with each other.

Additionally or alternatively, the controller circuit 102 may store the first and resultant ultrasound images 302, 404 in the memory 106. For example, the controller circuit 102 stores the first and resultant ultrasound images 302, 404 concurrently shown on the display 138 in the memory 106.

Figure 5:
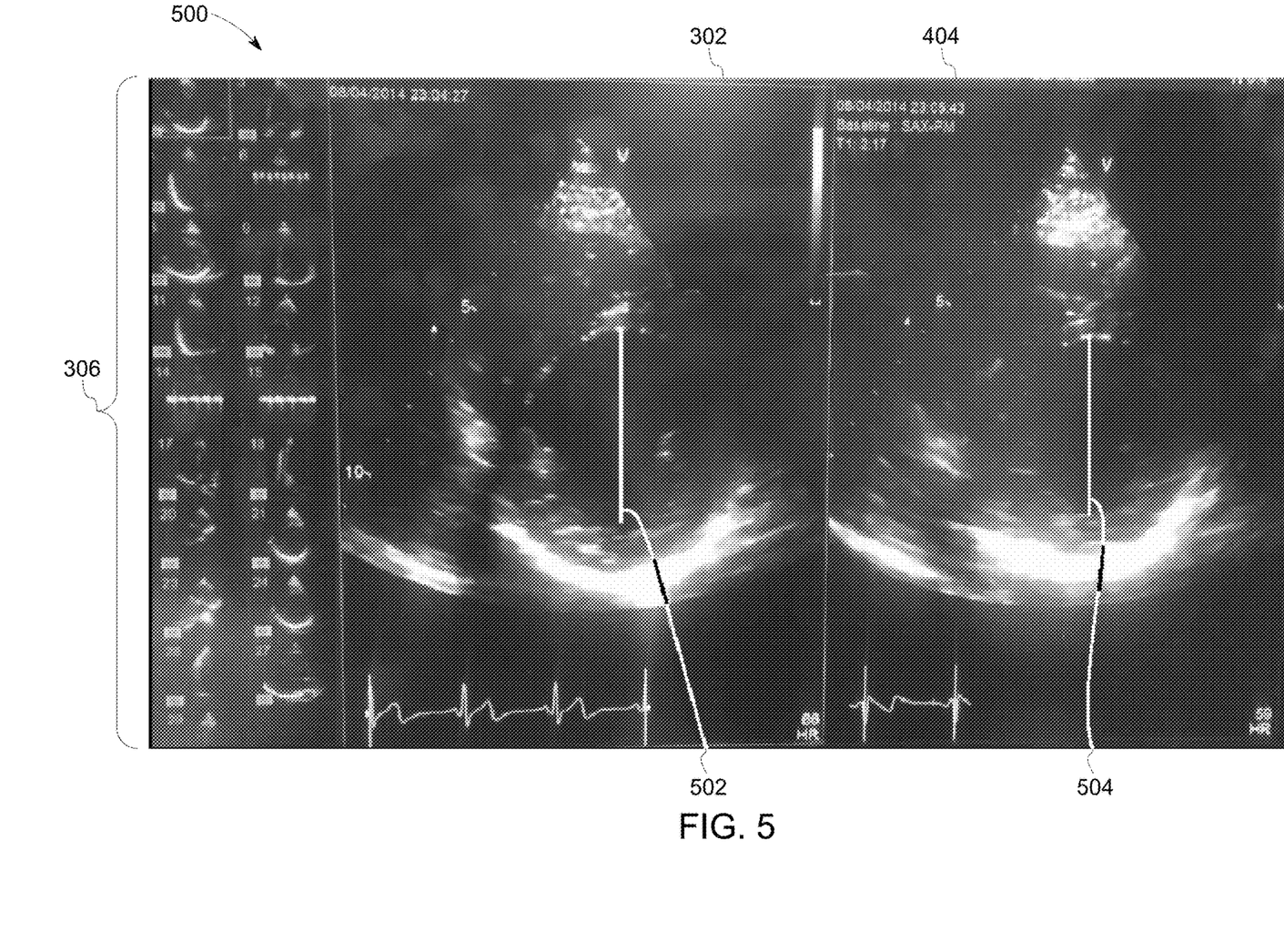
FIG. 5 illustrates a graphical user interface of current and resultant ultrasound images with anatomical measurements, according to an embodiment.

At 214, the controller circuit 102 determines whether the one or more resultant ultrasound images 404 includes anatomical measurements 504 (FIG. 5). For example, the resultant ultrasound image 402 may include the anatomical measurements 504 overlaid and/or included with the ultrasound data.

If the anatomical measurements 504 includes the anatomical measurements 504, then at 216, the controller circuit 102 displays the anatomical measurements 504 on the resultant ultrasound image 404. FIG. 5 illustrates a GUI 500 of current and resultant ultrasound images 302, 402 with anatomical measurements 502, 504, according to an embodiment. The resultant ultrasound image 402 includes the anatomical measurements 504. The anatomical measurements 504 are shown concurrently with the resultant ultrasound image 402. For example, the anatomical measurements 504 are overlaid on the resultant ultrasound image 402.

At 218, the controller circuit 102 overlays the anatomical measurements 504 on the current ultrasound image 302. For example, the controller circuit 102 overlays the anatomical measurements 504 on the current ultrasound image 302 as the anatomical measurements 502. The anatomical measurements 502 is shown on the current ultrasound image 302 in a common position as the anatomical measurements 504 relative to the resultant ultrasound image 404. For example, the controller circuit 102 determines a position of the anatomical measurements 504 relative to the related anatomical feature 406 (FIG. 4). The controller circuit 102 overlays the anatomical measurements 502 in a common position relative to the first anatomical feature 304 (FIG. 4). The anatomical measurements 502 enables the clinician to perform an anatomical measurement on the current ultrasound image 302 that matched the anatomical measurements 502.

For example, the anatomical measurements can be performed using diagnostic measurement tools. The diagnostic measurement tools are generated by the controller circuit 102. The diagnostic measurement tools are represented as a GUI having a plurality of user interface components. The plurality of user interface components represent types of anatomical measurements to be performed by the clinician. For example, the clinician using the user interface 142 may select the diagnostic measurement tools. The controller circuit 102 is configured to display the plurality of user interface components related to the tool on the display 138. The plurality of user interface components enable the clinician to perform one or more anatomical measurements. For example, one of the user interface components represent cursors. The clinician can position the cursors at to match the anatomical measurements 502 overlaid on the current ultrasound image 302. The controller circuit 102 stores the anatomical measurements in the memory 106.

Optionally, the controller circuit 102 may overlay the anatomical measurements for multiple resultant ultrasound images. For example, the controller circuit 102 identifies three resultant ultrasound images from three different prior ultrasound exams. The controller circuit 102 identifies the anatomical measurements for the three resultant ultrasound images. The controller circuit 102 overlays the three different anatomical measurements on the current ultrasound image 302. Optionally, the three different anatomical measurements may be distinct relative to each other to identify the corresponding resultant ultrasound image. For example, the three different anatomical measurements can be color coded, have different patterns (e.g., dashed, dotted, solid), and/or the like. Similar to the anatomical measurement 502, the three different anatomical measurements are shown on the current ultrasound image 302 in a common position as the anatomical measurement relative to the three resultant ultrasound images. For example, the controller circuit 102 determines a position of the anatomical measurements relative to the related anatomical features of the three different ultrasound images. The controller circuit 102 overlays the three different anatomical measurements in a common position relative to the anatomical feature. The three different anatomical measurements enables the clinician to perform an anatomical measurement on the current ultrasound image 302 that matches the three different anatomical measurements. It may be noted, that the controller circuit 102 may identify more than three resultant ultrasound images. Optionally, the controller circuit 102 may identify a plurality of resultant ultrasound images in a common prior ultrasound exam.

Additionally or alternatively, the clinician may select a trend. For example, the clinician using the user interface 142 selects a user interface component of the GUI shown on the displays 138 representing the trend. The controller circuit 102 can determined that the trend was received from the selection of the user interface component by the user interface 142. The trend is indicative of change in at least one of a pathology of interest, an anatomical measurement, an anatomical function, and/or the like between the current ultrasound exam and the prior ultrasound exams. Non-limiting examples of anatomical functions are a cardiovascular function (e.g., diastolic function, systolic function, cardiac cycle), a renal function, a digestive function, a metabolic function, a detoxification function, and/or the like. The anatomical function can be assessed to determine a disease and/or symptom of the patient for a clinical diagnosis. The controller circuit 102 is configured to identify differences between the pathology of interest, the anatomical measurement, the anatomical function between the current ultrasound image 302 and the resultant ultrasound image 404.

For example, the controller circuit 102 receives the anatomical measurement for the current ultrasound image 302 from the user interface 142. The controller circuit 102 compares the anatomical measurement of the current ultrasound image 302 with the anatomical measurement 504 of the resultant ultrasound image 404. The controller circuit 102 compares a position, magnitude, shape, and/or the like of the anatomical measurement 504 with the anatomical measurement received for the current ultrasound image 302. For example, the controller circuit 102 may overlay differences in the anatomical measurements of the current and resultant ultrasound images 302, 404. The controller circuit 102 may display the anatomical measurement 502 concurrently with the anatomical measurement received for the current ultrasound image 302. Optionally, the controller circuit 102 may overlay the difference in the position, magnitude, shape and/or the like representing the trend between the anatomical measurements on the current ultrasound image 302. The change in anatomical measurements between the current and resultant ultrasound images 302, 404 can indicate a change in the pathology of interest from the anatomical structure.

In another example, the trend may represent changes in the anatomical function. The controller circuit 102 compares the ultrasonic characteristics between the pairs of ultrasound images of the current and resultant ultrasound image 302, 404. The ultrasonic characteristics may correspond to differences in pixels of the ultrasound image mode of the pairs of the ultrasound images. For example, the anatomical function may be the cardiac function of the anatomical structure. The current and resultant ultrasound images 302, 404 were acquired during the Doppler ultrasound image mode. The controller circuit 102 compares the pixel colors representing the different quantified cardiac functions of the anatomical structure to determine a difference between the anatomical functions. For example, the difference may represent the difference in the quantified cardiac functions between the current and resultant ultrasound images 302, 404.

In an embodiment, a method (e.g., for identifying an ultrasound image between ultrasound exams) is provided. The method includes identifying a first ultrasound image feature of a current ultrasound image of an anatomical structure during a current ultrasound exam based on ultrasound data received from an ultrasound probe, and accessing a plurality of prior ultrasound images that were acquired during a prior ultrasound exam. The method includes comparing the first ultrasound image feature in the current ultrasound image with related anatomical features in the plurality of prior ultrasound images to identify candidate ultrasound images. The method includes identifying a resultant ultrasound image from the candidate ultrasound images based on the related ultrasound image features, and displaying the current and resultant ultrasound images on a display.

Optionally, the comparing operation includes determining a first set of characteristic vectors for the current ultrasound image and sets of related characteristic vectors for the plurality of prior ultrasound images. The first resultant ultrasound image being identified based on the first and related sets of characteristic vectors. Additionally or alternatively, the identifying operation of the first ultrasound image feature includes determining differences between the sets of characteristic vectors with the first set of characteristic vectors, and selecting the first resultant ultrasound image having a candidate difference within a predetermined non-zero threshold of the first set of feature vectors. Additionally or alternatively, the method includes displaying a graphical icon on the display indicative of an adjustment to the ultrasound probe to decrease the candidate difference.

Optionally, the first ultrasound image feature includes at least one of an anatomical measurement graphic, an ultrasound image mode, an anatomical feature, a view window, a noise of the current ultrasound image, or an acquisition setting.

Optionally, the comparing operation includes identifying tags of the plurality of prior ultrasound images, and selecting a set of ultrasound images from the plurality of prior ultrasound images having the tags indicative of the first ultrasound image feature. Additionally or alternatively, the candidate ultrasound images are in the set of ultrasound images.

Optionally, the first resultant ultrasound image includes an anatomical measurement, and the displaying operation includes displaying the anatomical measurement on the first resultant ultrasound image. Additionally or alternatively, the method includes overlaying the anatomical measurement on the current ultrasound image.

Optionally, the accessing operation includes receiving the plurality of prior ultrasound images along a bi-directional communication link.

Optionally, the anatomical structure includes at least one of a heart, a bone, a brain, a head, a bladder, a kidney, a liver, or a vascular structure.

Optionally, the identifying operation of the first resultant ultrasound image includes identifying a second resultant ultrasound image, and the displaying operation includes displaying the current ultrasound image, the first resultant ultrasound image, and the second resultant ultrasound image concurrently on the display.

In an embodiment, a system (e.g., a medical imaging system) is provided. The system includes an ultrasound probe configured to acquire ultrasound data of an anatomical structure, a display, and a controller circuit. The controller circuit is configured to identify a first ultrasound image feature of a current ultrasound image of the anatomical structure during a current ultrasound exam based on ultrasound data received from an ultrasound probe, access a plurality of prior ultrasound images that were acquired during a prior ultrasound exam, compare the first ultrasound image feature in the current ultrasound image with related ultrasound image features in the plurality of prior ultrasound images to identify candidate ultrasound images, identify a resultant ultrasound image from the candidate ultrasound images based on the related ultrasound image features, and display the current and resultant ultrasound images on the display.

Optionally, the controller circuit is configured to determine a first set of characteristic vectors for the current ultrasound image and sets of related characteristic vectors for the plurality of prior ultrasound images. The first resultant ultrasound image being identified based on the first and related sets of characteristic vectors. Additionally or alternatively, the controller circuit is configured to determine differences between the sets of characteristic vectors with the first set of characteristic vectors, and selecting the candidate ultrasound images having a candidate difference within a predetermined non-zero threshold of the first set of feature vectors. Additionally or alternatively, the controller circuit is configured to display a graphical icon on the display indicative of an adjustment to the ultrasound probe to decrease the candidate difference.

Optionally, the first ultrasound image feature includes at least one of an anatomical measurement graphic, an ultrasound image mode, an anatomical feature, a view window, a noise of the current ultrasound image, or an acquisition setting.

Optionally, the controller circuit is configured to identify tags of the plurality of prior ultrasound images, and selecting a set of ultrasound images from the plurality of prior ultrasound images having the tags indicative of the first ultrasound image feature. Additionally or alternatively, the candidate ultrasound images are in the set of ultrasound images.

Optionally, the controller circuit is configured to identify a second resultant ultrasound image such that the controller circuit displays the current ultrasound image, the first resultant ultrasound image, and the second resultant ultrasound image concurrently on the display.

In an embodiment, a method (e.g., for identifying an ultrasound image between ultrasound exams) is provided. The method includes identifying a first ultrasound image feature of a current ultrasound image of an anatomical structure during a current ultrasound exam based on ultrasound data received from an ultrasound probe. The first ultrasound image feature includes at least one of an anatomical measurement graphic, an ultrasound image mode, an anatomical feature, a view window, a noise of the current ultrasound image, or an acquisition setting. The method includes accessing a plurality of prior ultrasound images of the anatomical structure that were acquired during a prior ultrasound exam, comparing the first ultrasound image feature with related ultrasound image features in the plurality of prior ultrasound images to identify candidate ultrasound images, and determining a first set of characteristic vectors for the first ultrasound image and sets of related characteristic vectors for the plurality of prior ultrasound images. The candidate ultrasound image is identified based on the first and related sets of characteristic vectors. The method includes identifying first and second resultant ultrasound images from the candidate ultrasound images based on the related ultrasound image features, and displaying the current, the first resultant, and the second resultant ultrasound images on the display.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A tangible and non-transitory computer readable medium comprising one or more computer software modules configured to direct one or more processors to:
identify first ultrasound image features of a current ultrasound image during a current ultrasound exam based on ultrasound data received from an ultrasound probe;
access a plurality of prior ultrasound images that were acquired during a prior ultrasound exam;
compare the first ultrasound image features of the current ultrasound image with related ultrasound image features in the plurality of prior ultrasound images after identifying the first ultrasound image features of the current ultrasound image, wherein the first ultrasound image features comprise an ultrasound image mode and at least one anatomical structure, wherein the at least one anatomical structure is selected from the group consisting of a heart, a tissue of the heart, and a vascular structure of the heart, and wherein the related ultrasound image features comprise at least one corresponding ultrasound image mode and at least one corresponding anatomical structure;
identify, after identifying the first ultrasound image features of the current ultrasound image, a first resultant ultrasound image from the plurality of prior ultrasound images based on the comparison of the first ultrasound image features in the current ultrasound image with related ultrasound image features in the plurality of prior ultrasound images, the first resultant ultrasound image having at least one anatomical structure having a common orientation with the at least one anatomical structure of the current ultrasound image; and
display the current ultrasound image and the first resultant ultrasound image that was identified from the plurality of prior ultrasound images on a display.

2. The tangible and non-transitory computer readable medium of claim 1, wherein the comparing operation includes determining a first set of characteristic vectors for the current ultrasound image and sets of related characteristic vectors for the plurality of prior ultrasound images, wherein the first set of characteristic vectors and the sets of related characteristic vectors include values for intensity, color, and gradient of individual pixels, and wherein the first resultant ultrasound image is identified based on the first set of characteristic vectors and the related sets of characteristic vectors.

3. The tangible and non-transitory computer readable medium of claim 2, wherein the identifying operation of the first ultrasound image feature includes determining differences between the related sets of characteristic vectors for the plurality of prior ultrasound images with the first set of characteristic vectors for the current ultrasound image, and selecting the first resultant ultrasound image having a candidate difference within a predetermined non-zero threshold of the first set of feature vectors.

4. The tangible and non-transitory computer readable medium of claim 1, wherein the first ultrasound image features further include at least one of an anatomical measurement graphic, a view window, a noise of the current ultrasound image, or an acquisition setting.

5. The tangible and non-transitory computer readable medium of claim 1, wherein the comparing operation includes identifying tags of the plurality of prior ultrasound images and selecting a set of ultrasound images from the plurality of prior ultrasound images having the tags indicative of the first ultrasound image features.

6. The tangible and non-transitory computer readable medium of claim 5, wherein the first resultant ultrasound image is in the set of ultrasound images.

7. The tangible and non-transitory computer readable medium of claim 1, wherein the first resultant ultrasound image includes an anatomical measurement, and wherein the displaying operation includes displaying the anatomical measurement on the first resultant ultrasound image.

8. The tangible and non-transitory computer readable medium of claim 7, wherein the one or more computer software modules are further configured to direct the one or more processors to overlay the anatomical measurement on the current ultrasound image.

9. The tangible and non-transitory computer readable medium of claim 1, wherein the accessing operation includes receiving the plurality of prior ultrasound images along a bi-directional communication link.

10. The tangible and non-transitory computer readable medium of claim 1, wherein the one or more computer software modules are further configured to direct the one or more processors to identify a second resultant ultrasound image, and to display the current ultrasound image, the first resultant ultrasound image, and the second resultant ultrasound image concurrently on the display.

11. A medical imaging system comprising:
an ultrasound probe configured to acquire ultrasound data of an anatomical structure;
a display; and
a controller circuit configured to:
identify first ultrasound image features of a current ultrasound image during a current ultrasound exam based on ultrasound data received from an ultrasound probe;
access a plurality of prior ultrasound images that were acquired during a prior ultrasound exam;
compare the first ultrasound image features of the current ultrasound image with related ultrasound image features in the plurality of prior ultrasound images after identifying the first ultrasound image features of the current ultrasound image, wherein the first ultrasound image features comprise an ultrasound image mode and at least one anatomical structure, wherein the at least one anatomical structure is selected from the group consisting of a heart, a tissue of the heart, and a vascular structure of the heart, and wherein the related ultrasound image features comprise at least one corresponding ultrasound image mode and at least one corresponding anatomical structure;
identify, after identifying the first ultrasound image features of the current ultrasound image, a first resultant ultrasound image from the plurality of prior ultrasound images based on the comparison of the first ultrasound image features in the current ultrasound image with related ultrasound image features in the plurality of prior ultrasound images, the first resultant ultrasound image having at least one anatomical structure having a common orientation with the at least one anatomical structure of the current ultrasound image; and display the current ultrasound image and the first resultant ultrasound image that was identified from the plurality of prior ultrasound images on the display.

12. The medical imaging system of claim 11, wherein the controller circuit is further configured to determine a first set of characteristic vectors for the current ultrasound image and sets of related characteristic vectors for the plurality of prior ultrasound images, the first resultant ultrasound image being identified based on the first set of characteristic vectors and the related sets of characteristic vectors, wherein the first set of characteristic vectors and the sets of related characteristic vectors include values for intensity, color, and gradient of individual pixels.

13. The medical imaging system of claim 11, wherein the controller circuit is further configured to determine differences between the sets of related characteristic vectors with the first set of characteristic vectors, and to select the first resultant ultrasound image having a candidate difference within a predetermined non-zero threshold of the first set of feature vectors.

14. The medical imaging system of claim 13, wherein the controller circuit is further configured to display a graphical icon on the display indicative of an adjustment to the ultrasound probe to decrease the candidate difference.

15. The medical imaging system of claim 11, wherein the first ultrasound image features further include at least one of an anatomical measurement graphic, a view window, a noise of the current ultrasound image, or an acquisition setting.

16. The medical imaging system of claim 11, wherein the controller circuit is configured to identify tags of the plurality of prior ultrasound images, and the controller circuit is configured to select a set of ultrasound images from the plurality of prior ultrasound images having the tags indicative of the first ultrasound image feature, wherein the first resultant ultrasound image is in the set of ultrasound images.

17. The medical imaging system of claim 11, wherein the controller circuit is configured to identify a second resultant ultrasound image and to display the current ultrasound image, the first resultant ultrasound image, and the second resultant ultrasound image concurrently on the display.

18. A tangible and non-transitory computer readable medium comprising one or more computer software modules configured to direct one or more processors to:

identify first ultrasound image features of a current ultrasound image of an anatomical structure during a current ultrasound exam based on ultrasound data received from an ultrasound probe, wherein the first ultrasound image features comprise an ultrasound image mode and at least one anatomical structure, wherein the at least one anatomical structure is selected from the group consisting of a heart, a tissue of the heart, and a vascular structure of the heart;

access a plurality of prior ultrasound images of the anatomical structure that were acquired during a prior ultrasound exam;

compare the first ultrasound image features in the current ultrasound image with related ultrasound image features in the plurality of prior ultrasound images after identifying the first ultrasound image features of the current ultrasound image, wherein the related ultrasound image features comprise at least one corresponding ultrasound image mode and at least one corresponding anatomical structure;

determine a first set of characteristic vectors for the current ultrasound image and sets of related characteristic vectors for the plurality of prior ultrasound images; and identify, after identifying the first ultrasound image features of the current ultrasound image, a first resultant ultrasound image and a second resultant ultrasound image from the plurality of prior ultrasound images and the sets of related characteristic vectors based on the comparison of the first ultrasound image features in the current ultrasound image with related ultrasound image features in the plurality of prior ultrasound images, the first resultant ultrasound image and the second resultant ultrasound image each having at least one anatomical structure that has a common orientation with the at least one anatomical structure of the current ultrasound image.

* * * * *